(12) United States Patent
Vignon et al.

(10) Patent No.: US 10,376,234 B2
(45) Date of Patent: Aug. 13, 2019

(54) ULTRASONIC IMAGING APPARATUS AND A METHOD FOR IMAGING A SPECULAR OBJECT AND A TARGET ANATOMY IN A TISSUE USING ULTRASOUND

(71) Applicant: KONINKLIJKE PHILIPS N.V., Eindhoven (NL)

(72) Inventors: Francois Guy Gerard Marie Vignon, Eindhoven (NL); Jin Chang, Eindhoven (NL); Allison Arden Daniels, Eindhoven (NL); Ameet Kumar Jain, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 423 days.

(21) Appl. No.: 14/399,635

(22) PCT Filed: May 6, 2013

(86) PCT No.: PCT/IB2013/053615
§ 371 (c)(1),
(2) Date: Nov. 7, 2014

(87) PCT Pub. No.: WO2013/168076
PCT Pub. Date: Nov. 14, 2013

(65) Prior Publication Data
US 2015/0119701 A1    Apr. 30, 2015

Related U.S. Application Data

(60) Provisional application No. 61/645,674, filed on May 11, 2012.

(51) Int. Cl.
*A61B 8/14* (2006.01)
*A61B 8/08* (2006.01)
*A61B 8/00* (2006.01)
*G09G 5/38* (2006.01)
*A61B 34/20* (2016.01)
*A61B 90/00* (2016.01)

(52) U.S. Cl.
CPC .............. *A61B 8/0841* (2013.01); *A61B 8/14* (2013.01); *A61B 8/4416* (2013.01); *A61B 8/463* (2013.01);
(Continued)

(58) Field of Classification Search
None
See application file for complete search history.

(56) References Cited

U.S. PATENT DOCUMENTS 6,048,312 A * 4/2000 Ishrak ................. A61B 8/0833
128/916
6,336,899 B1    1/2002 Yamazaki
(Continued)

FOREIGN PATENT DOCUMENTS

| EP | 1281368 | 2/2003 |
|---|---|---|
| WO | 2008126015 | 10/2008 |
| WO | 2010125505 A1 | 11/2010 |

OTHER PUBLICATIONS

"Enhancement of Needle Visibility in Ultrasound Guided Percutaneous Procedures" Cheung et al, Ultr. Med Bios. 2004 30; 617-624.

*Primary Examiner* — Mark D Remaly

(57) ABSTRACT

The invention relates to a method and an ultrasonic imaging apparatus (20) for imaging a specular object (such as a biopsy needle) and a target anatomy in a tissue, whereby the specular object remains visible even when its location deviates from a target plane (21) including the target anatomy.

16 Claims, 4 Drawing Sheets

(52) U.S. Cl.
CPC .......... *A61B 8/483* (2013.01); *A61B 8/5246* (2013.01); *G09G 5/38* (2013.01); *A61B 8/466* (2013.01); *A61B 8/523* (2013.01); *A61B 2034/2063* (2016.02); *A61B 2090/378* (2016.02); *G06T 2207/10132* (2013.01); *G06T 2207/30004* (2013.01); *G09G 2340/12* (2013.01)

(56) References Cited

U.S. PATENT DOCUMENTS

| | | | |
|---|---|---|---|
| 6,530,885 B1* | 3/2003 | Entrekin | G01S 7/52053 128/916 |
| 6,623,432 B2* | 9/2003 | Powers | A61B 8/06 128/916 |
| 6,733,458 B1* | 5/2004 | Steins | A61B 8/0833 600/461 |
| 2002/0173719 A1* | 11/2002 | Zhao | A61B 8/0833 600/437 |
| 2005/0152807 A1 | 7/2005 | Osterloh | |
| 2007/0100234 A1* | 5/2007 | Arenson | A61B 6/032 600/429 |
| 2009/0024039 A1* | 1/2009 | Wang | A61B 10/0233 600/459 |
| 2009/0306511 A1 | 12/2009 | Yamagata | |
| 2010/0168580 A1* | 7/2010 | Thiele | G01S 7/52085 600/447 |
| 2013/0225984 A1* | 8/2013 | Cheng | A61B 8/0841 600/424 |

* cited by examiner

ULTRASONIC IMAGING APPARATUS AND A METHOD FOR IMAGING A SPECULAR OBJECT AND A TARGET ANATOMY IN A TISSUE USING ULTRASOUND

This application is the U.S. National Phase application under 35 U.S.C. § 371 of International Application No. PCT/IB2013/053615, filed on May 6, 2013, which claims the benefit of U.S. Provisional Application No. 61/645,674 filed on May 11, 2012. These applications are hereby incorporated by reference herein.

FIELD OF THE INVENTION

The invention relates to a method of imaging a specular object, such as for example a needle-like instrument, and a target anatomy in a tissue using ultrasound, the method comprising a tissue imaging step of transmitting first sound waves into a volumetric region of the tissue, the volumetric region including the target anatomy located in a target plane, of receiving echoes of said first sound waves from the target plane, and of processing said received echoes to produce a tissue image, said tissue imaging step using a tissue mode specific set of parameters, and a specular object imaging step of transmitting second sound waves into said volumetric region of the tissue, the volumetric region including the specular object, of receiving echoes of said second sound waves from the target plane, and of processing said received echoes to produce a specular object image, said specular object imaging step using a specular object mode specific set of parameters, and a display step of displaying a combined tissue image and specular object image.

The invention further relates to an apparatus implementing the method according to the invention.

More specifically the invention relates to a method of imaging a biopsy needle using ultrasound and to an ultrasonic imaging apparatus for imaging a biopsy needle.

BACKGROUND OF THE INVENTION

Ultrasound is commonly used for imaging needle insertion during interventional surgical procedures. Such needles may, for example, be paracentetic needles for withdrawal of fluid from a target anatomy in a body or biopsy needles for the removal of samples from a target anatomy in a body. Needles may also be used to administer drugs or other substances into a specific location relative to a target anatomy in the body.

During such procedures the precision of needle trajectory is highly important. The needle should not disturb or damage anatomy not connected with the procedure being undertaken. Some procedures may be directed towards small regions in the body e.g. artery or an area close to a major anatomy, such as the heart. Accuracy of needle placement is therefore vital.

Ultrasound is often used as an imaging method for imaging a needle and a target anatomy in support of the interventional procedure. Other imaging alternatives, such as Xray or EM (electromagnetic) guidance, suffer from drawbacks such as risk of radiation exposure, 2D view only, additional set-up time, tracking errors or lack of visibility of the specular object, such as a biopsy needle.

A method according to the preamble for imaging a specular needle together with a target anatomy in a tissue is described in "Enhancement of needle visibility in ultrasound-guided percutaneous procedures"; Cheung and Rohling's; Ultr. Med. Biol. (2004) 30: 617-624. Here the visualization of a needle in the ultrasound image is enhanced, without compromising the quality of the visualization of the target anatomy in the tissue, by displaying the combination of a specular object image (also referred to as a needle-specific image) and a tissue image. The tissue image, obtained using a tissue mode specific set of parameters, depicts the target anatomy in the tissue but may depict the needle in a poor quality, or even do not depict the needle at all, whereas the specular object image, obtained using a specular object mode specific set of parameters, depicts the needle with great contrast, but may depict almost no background tissue. Combining both images, by taking their weighted average, yield an image (often referred to as a needle-enhanced image) showing both the needle and the target anatomy.

The characteristics of the ultrasound imaging in the tissue imaging step and in the specular object imaging step are optimized to allow the best possible responses. These characteristics are set by using respectively the tissue mode specific set of parameters or the specular object mode specific set of parameters. These sets of parameters may comprise, for example, the frequency of the ultrasound waves, beam steering and beam density related parameters, the focal depth, the rate at which the echoes are received (the frame rate), and parameters controlling the type of processing of the received echoes, such as for example aperture processing and temporal filtering.

In the above described method the favored geometry for the needle to be displayed is the so-called "in-plane" geometry wherein the long axis of the needle is contained in the target plane including the target anatomy. However, in a significant number of cases the needle location deviates from the target plane due to, for example, tissue heterogeneities and bevel asymmetry.

It is now a problem of the known method that such an out-of-plane needle is not shown (or not sufficiently shown) in the combined (needle-enhanced) images. The clinician has to move the imaging transducer, transmitting and receiving the sound waves, to locate the needle, but then loses the target anatomy located in the original target plane. Furthermore, since the clinician does not know where the needle is located in relation to the original target plane, he has no indication how to move the transducer to find the needle.

SUMMARY OF THE INVENTION

It is an object of the present invention to overcome the above problems of the prior art. According to the present invention this object is achieved by providing a method according to the preamble in which the specular object imaging step is adapted i) to receive echoes of said second sound waves from a plurality of image planes, said plurality of image planes separated in an elevation direction at selected elevations around the target plane, and ii) to process the echoes received from the target plane and from the plurality of image planes to produce the specular object image.

The inventors have realized that it is important to keep imaging the target plane including the target anatomy in the tissue imaging step, and at the same time image a volumetric region of the tissue surrounding that target anatomy without a need to move the transducer in the specular object imaging step.

According to the invention a plurality of image planes separated in an elevation direction is acquired in the specular object imaging step using the specular object mode specific set of parameters. This gives a 3-dimensional set of (needle-specific) images. From this 3-dimensional set of (needle-specific) images the specular object image is obtained providing a detailed image of the object (such as a needle) which can be pinpointed in three dimensions and quantified in length and direction.

The plurality of image planes may comprise the target plane including the target anatomy. This target plane may fall in the centre of the plurality of image planes, but this is not essential. Nor it is essential to centre an apex of the elevation planes at the centre of the array transducer producing the ultrasound waves, or for the elevation planes to be parallel.

In the tissue imaging step a 2-dimensional tissue image of the target anatomy located in a target plane is obtained, while in the specular object imaging step the specular object image (such a a needle) is obtained from a 3-dimensional set of (needle-specific) images. Thus the relation between them allows combining of these images to display the combined (needle-enhanced) image in which the object (such as a needle) is shown in relation to the target anatomy. Such a combined image allows the operator to see the object (such as a needle) even when it does not directly coincide with the target plane. It should be noted that it is advantageous that these images have been obtained without moving the transducer.

In the display step the planar tissue image (showing the target anatomy) is combined with a volumetric rendering of the specular object. In this way a simultaneous display of the specular object together with the target anatomy is maintained, even when the specular object moves away from the target plane.

The data from the individual planes in the plurality of image planes may be combined by averaging to form the specular object image. However, in an embodiment a 3-dimensional segmentation algorithm is used to segment the specular object (such as a needle) out of the plurality of image planes to create a specular object image only showing that object. In a further embodiment each of the planes in the plurality of image planes are used as individual snapshots to produce separate images showing (part of) the specular object which are then fitted together in jigsaw-like fashion.

According to the invention a plurality of image planes separated in an elevation direction at selected elevations around the target plane are acquired in the specular object imaging step. It is noted that the target plane may fall in the centre of the plurality of image planes (resulting in image planes symmetrically arranged about the target plane), but that this is not essential to the present invention. The angular range of elevation of many commercially available array transducers may be as much wide as +45 to −45 degrees. If the elevation planes are parallel to each other, the lateral range spanned by all the planes may be as wide as the elevational probe footprint. According to an embodiment of the present invention a range between −10 degrees and +10 degrees in relation to the target plane is preferred. Such a range has been found to be most efficient in terms of imaging quality and imaging rate, while at the same time being large enough to capture the specular object. For the same reasons an imaging range between −15 mm to +15 mm is preferred when a plurality of parallel image planes is acquired (using, for example, a linear array transducer) in the specular object imaging step.

In a further embodiment of the present invention the image planes in the plurality of image planes are being imaged in the specular object imaging step at a lower imaging rate than the imaging rate at which the target plane is being imaged in the tissue imaging step. This allows for maintaining an optimized frame rate for displaying the combined tissue end specular object image without undue burden on the image processor hardware. The tissue image is preferably imaged at a high imaging rate to give a real-time and most detailed image of the tissue in the target plane. The specular object image needs less detail and thus a lower imaging rate of the plurality of images from which this specular object image is derived is possible.

A further embodiment of the present invention involves multiple tissue imaging steps and multiple specular object imaging steps which are performed in an interleaved manner. This embodiment has the advantage that it reduces any temporal lag between the tissue image and the specular object image.

The object of the present invention is further achieved by providing an ultrasonic imaging apparatus for of imaging a specular object and a target anatomy in a tissue, the apparatus comprising an array transducer for transmitting sound waves into a volumetric region of the tissue and for receiving echoes of said sound waves, said array transducer adapted to have elevation steering capabilities;

a beamformer for controlling the transmission of sound waves by the array transducer such that first sound waves are transmitted into the volumetric region including the target anatomy located in a target plane and echoes are received of said first sound waves from the target plane, and for controlling the transmission of sound waves by the array transducer such that second sound waves are transmitted into the volumetric region including the specular object and echoes are received of said second sound waves from the target plane, said beamformer adapted to control the reception of said second sound waves from a plurality of image planes, said plurality of image planes separated in an elevation direction at selected elevations around the target plane;

a data processor for processing said received echoes of said first sound waves to produce a tissue image and for processing said received echoes of said second sound waves to produce a specular object image, said data processor adapted to process the echoes received from the target plane and from the plurality of image planes to produce the specular object image; and an image processor for displaying a combined tissue image and specular object image.

It is noted that the data processor and the image processor may be formed by dedicated hardware as well as by a generic processor implementing the required functions through appropriate firmware.

It is noted that international patent application WO 2008/126015 describes an ultrasonic diagnostic imaging system that scans a plurality of planar slices in a volumetric region which are parallel to each other. The image data of the individual slices is combined by projecting the data in the elevation dimension to produce a so-called "thick slice" image. The thick slice image is then displayed at a high frame rate by combining a single newly acquired slice with slices previously acquired. The described method thus aims at providing, in the tissue imaging step, spatially compounded images which can be generated at a high frame rate.

BRIEF DESCRIPTION OF THE FIGURES

The principle of the invention and preferred embodiments thereof will be further elucidated with reference to the figures, where.

DETAILED DESCRIPTION OF THE INVENTION

Figure 1A:
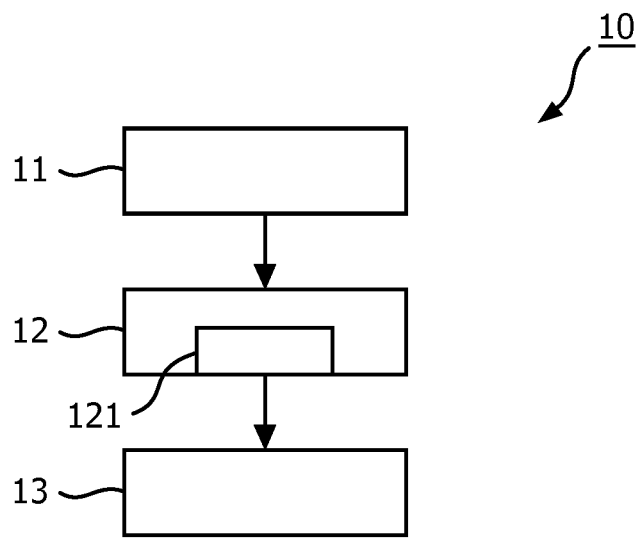
FIGS. 1A and 1B show flowcharts of embodiments of the method according to the invention.

FIG. 1A illustrates an embodiment 10 of the method according to the invention. The embodiment 10 comprises a tissue imaging step 11 of transmitting first sound waves into a volumetric region 22, of receiving echoes of said first sound waves from a target plane 21 (said target plane including the target anatomy), and of processing said received echoes to produce a tissue image. In this tissue imaging step 11a tissue mode specific set of parameters is used, thereby ensuring the optimal imaging of the target anatomy in the tissue. The embodiment 10 further comprises a specular object imaging step 12 of transmitting second sound waves into said volumetric region 22, of receiving echoes of said second sound waves from a plurality of image planes 24, 25 separated in an elevation direction at selected elevations around the target plane 21, and of processing the echoes received from the target plane and from the plurality of image planes to produce a specular object image. In this specular object imaging step 12 a specular object mode specific set of parameters is used, thereby ensuring the optimal imaging of the specular object, such as for example a needle. In a display step 13 of the embodiment 10 both the tissue image and the specular object image (often referred to as a so-called needle-specific image) are combined into a single image (often referred to as a so-called needle-enhanced image) for display.

In a further embodiment the specular object imaging step 12 comprises a segmentation sub-step 121. In this segmentation sub-step the specular object is segmented out of each individual plane of the plurality of image planes. In the specular object imaging step 12 the specular object image is than created out of the segmented individual planes.

Figure 1B:
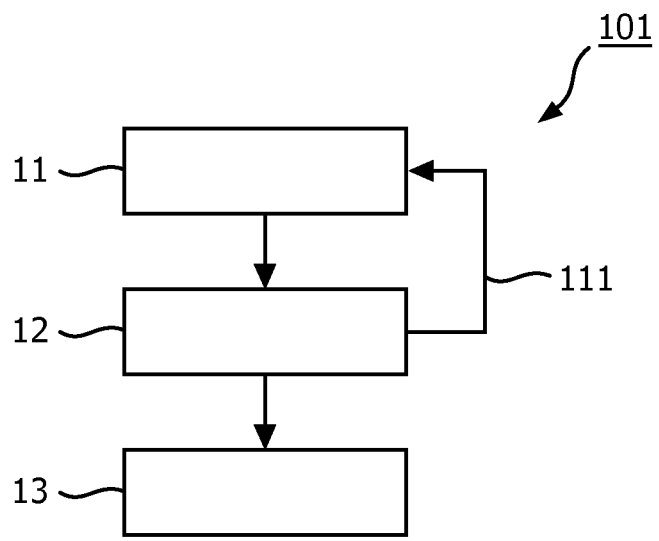

FIG. 1B illustrates an alternative embodiment 101 of the method according to the invention. This embodiment 101 comprises the tissue imaging step 11, the specular object imaging step 12 and the display step 13 as described above with reference to FIG. 1A. However, the tissue imaging step 11 and the specular object imaging step 12 are performed multiple times and in an interleaved manner, as is indicated by loop 111. First a tissue image of the target plane 21 is imaged. Next a first plurality of image planes is imaged. This first plurality of images planes consist, for example, of the three image planes around the target plane 21. Next a subsequent tissue image of the target plane 21 is imaged, after which a second plurality of image planes is imaged. This second plurality of images planes consisting, for example, of three image planes adjacent to the first plurality of image planes. This loop 111 continues until all of the planes in the plurality of images planes are imaged. It is noted that the plurality of image planes may be subdivide in alternative ways and that it is even not necessary that the planes in the plurality of images planes are imaged sequentially. In a further embodiment the tissue image of the target plane 21 is combined in display step 13 with the last available specular object image each time such a tissue image is imaged in one of the tissue imaging steps 11.

Figure 2:
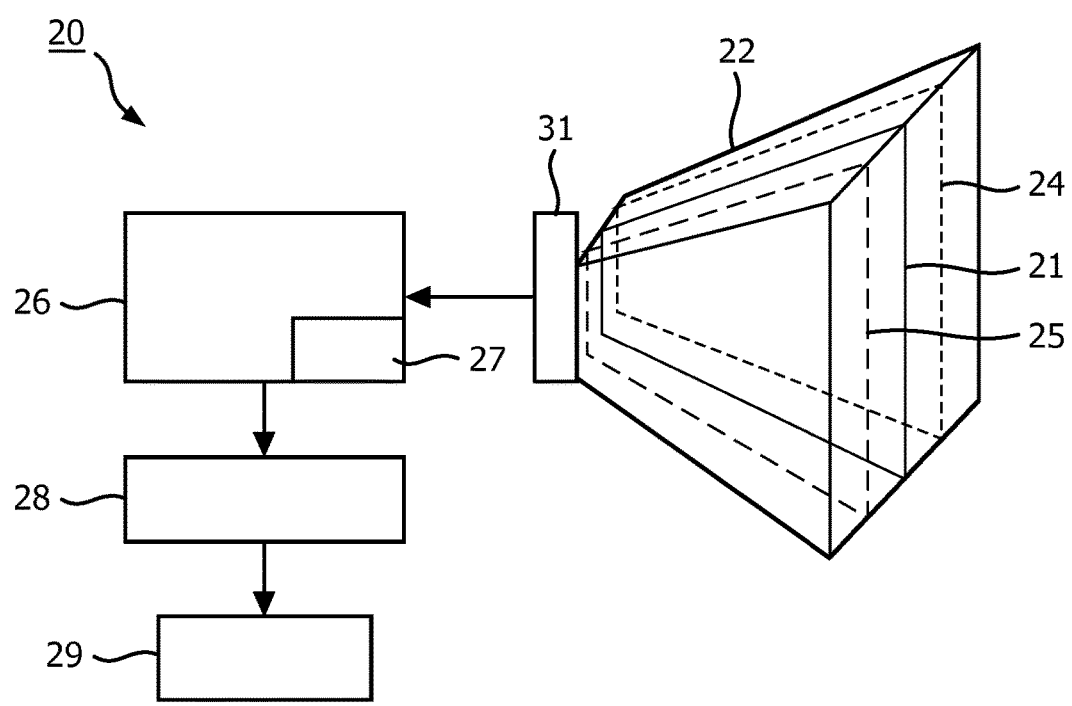
FIG. 2 schematically illustrates part of an ultrasound imaging apparatus according to the invention.

FIG. 2 illustrates part of an ultrasound imaging apparatus according to the invention implementing an embodiment of the above described method according to the invention. An array transducer 31 insonifies a volumetric region 22 including a target anatomy with ultrasound. The volumetric region 22 comprises a two dimensional target plane 21 and a plurality of image planes, here illustrated by two image planes 24, 25 located immediately adjacent to and on opposite sides of the target plane 21. The incident ultrasound from the array transducer 31 is shaped and controlled by a beamformer 26. The beamformer 26 provides capability for generating a 2-dimensional tissue image of the target plane 21 by using parameters from a tissue mode specific set of parameters and capability for generating a 3-dimensional plurality of image planes 24, 25 by using parameters from a specular object mode specific set of parameters. The beamformer comprises a module 27 which provides the capability to image elevation planes, such as planes 24 and 25, at different angular and/or lateral elevations. Ultrasound returned and received by the ultrasound array transducer 31 is fed to a data processor 28 for producing a tissue image and for producing a specular object image. These two images are fed to an image processor 29 for displaying a combined tissue image and specular object image.

In an embodiment the data processor 28 is adapted to segment the specular object out of the plurality of image planes to produce a specular object image only showing that object. To this end the data processor 28 may include dedicated hardware tailored to this segmentation process.

Figure 3A:
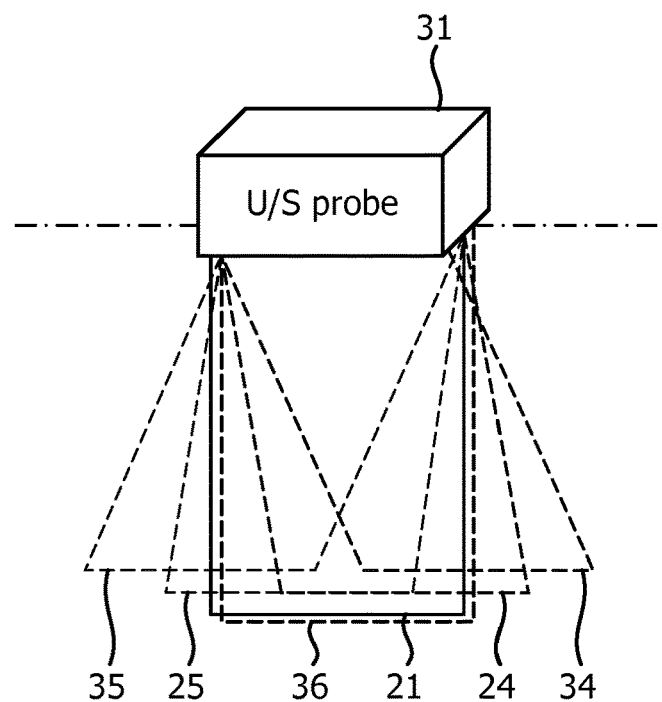
FIGS. 3A, 3B and 3C illustrate how the various images are obtained according to an embodiment of the invention

FIG. 3A shows an array transducer 31 and the target plane 21 and the plurality of image planes 24, 25, 34 and 35. The target plane 21 is imaged in the tissue imaging step 11 to produce the tissue image. The plurality of image planes 24, 25, 34 and 35 are imaged in the specular object imaging step 12. According to this embodiment the target plane 21 is also imaged in the specular object imaging step, now using the specular object specific set of parameters. This is represented by the further image plane 36, which coincident with the target plane 21.

Figure 3B:
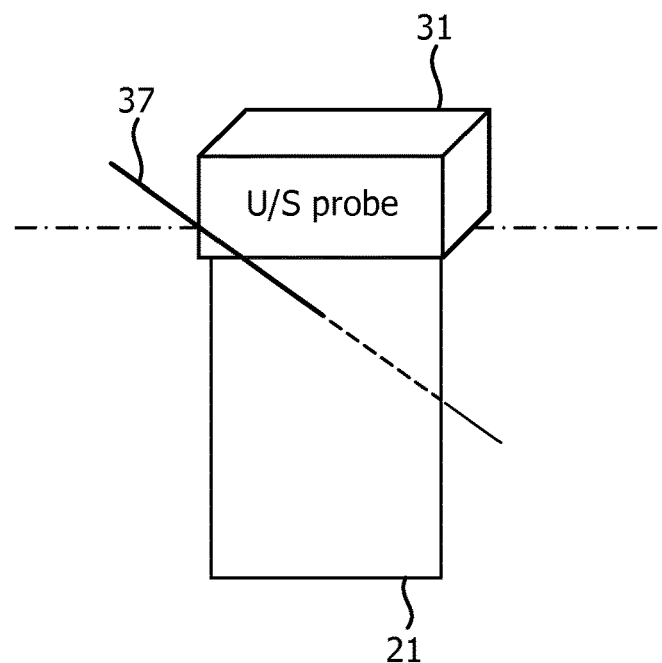

FIG. 3B shows the array transducer 31 and the target plane 21 in relation to a needle 37. It can be seen from the figure that the needle is not aligned with the target plane 21 and does not lie completely along the target plane 21, but sits at an angle relative to it. The solid line of the needle 37 is indicative of the part of the needle in front of the target plane 21, while the dashed line is indicative of the part of the needle lying behind the target plane 21.

Figure 3C:
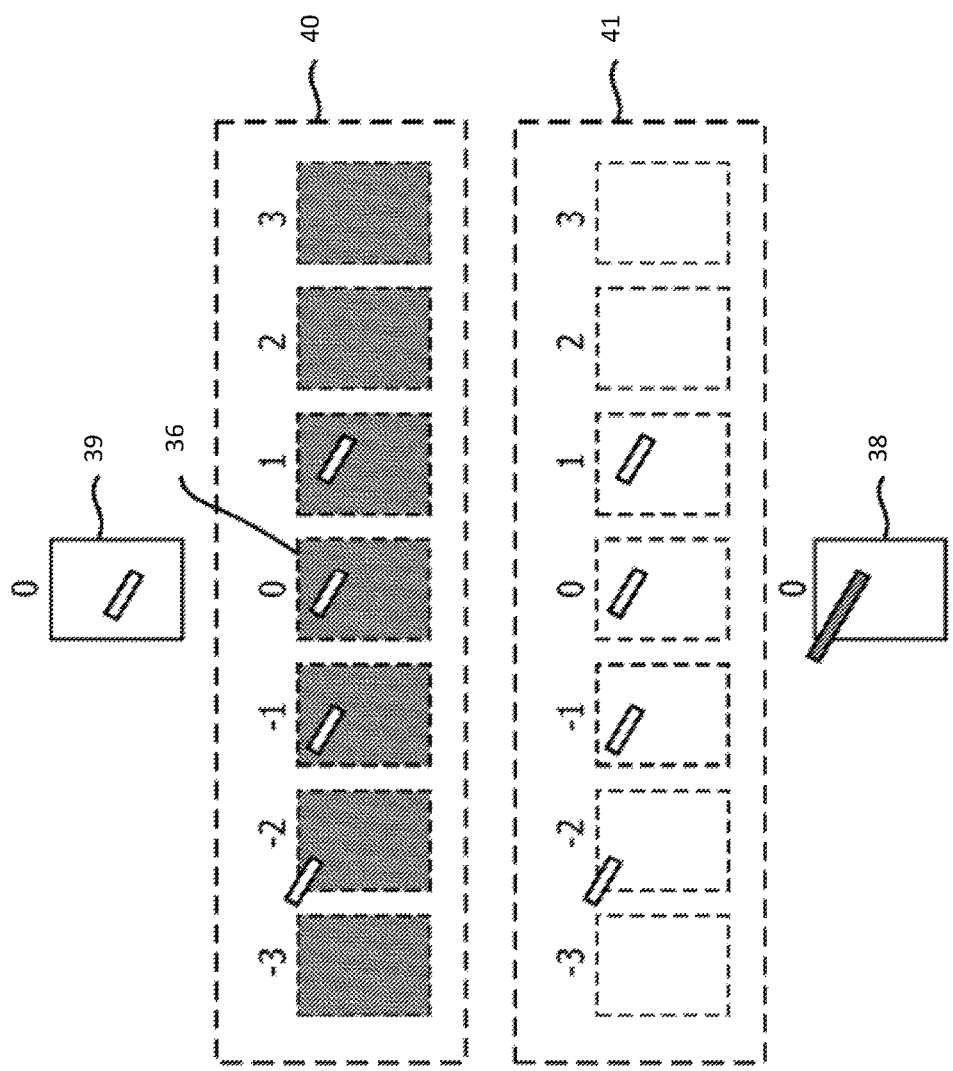

FIG. 3C illustrates the images obtained in the various steps according to the invention when visualizing such an out-of-plane needle as is depicted in FIG. 2B. In the tissue imaging step 11a tissue image 39 of the target plane 21 is obtained. Next a plurality 40 of image planes is obtained for several elevations in the specular object imaging step 12. Here it has been chosen to have the target plane itself (represented by the further image plane 36) and three elevations in the positive angular direction and three in the negative angular direction with respect to the target plane 21. The target plane location represented by the further image plane 36 is labeled with a zero in the figure and the elevated image planes with a positive or negative one, two or three. It is noted that this number of elevated image planes is merely an example and should not be construed as limiting. In display step 13 the tissue image 39 and the plurality 40 of image planes are combined into a final image 38 to be displayed. This combination can be done by overlaying the 3-dimensional image information from the plurality 40 of image planes on the 2-dimensional tissue image. Alternatively, this combination can be done by first combining the 3-dimensional image information from the plurality 40 of image planes into a specular object image and subsequently overlaying this specular object image on the tissue image. The information from the individual planes in the plurality 40 of image planes may, for example, be combined by averaging to form the specular object image. It is noted that the combination of the images into a final image 38 to be displayed is not limited to overlay techniques only, but that other techniques, including showing the tissue image and the specular object image alongside each other, may be used as well.

An embodiment of the invention involves an optional segmentation sub-step 121. In this sub-step a plurality 41 of segmentation images is made available over the same range as for the plurality 40 of image planes. Known segmentation algorithms can be used to segment the specular object (such as the needle in this example) out of the plurality 40 of image planes to form the plurality 41 of segmentation images. In the display step 13 the tissue image 39 and the plurality 41 of segmentation image are now combined into the final image 38. Alternatively, the plurality 41 of segmentation images are combined into a specular object image only showing that object (such as the needle in this example).

As can be seen in FIG. 3B the needle does not lie completely along the target plane 21, but sits at an angle relative to it. Part of the needle is in front of the target plane 21, while part of the needle is behind the target plane 21. This results in each individual image plane in the plurality 40 of image planes showing (part of) the needle in a different location in said individual image plane, as is shown in FIG. 3C.

In an embodiment of the invention the needle (more in general, the specular object) as shown in the combined final image 38 is coded depending on the position deviation of the individual image planes from the target plane 21. Each part of the needle originating from a different individual image plane has a different coding in the reconstructed needle shown in the combined final image 38. A preferred coding technique is color coding the needle, since the use of color is easy to absorb and understand by an operator. A an example, the part of the needle shown in the combined final image 38 originating from the individual image planes in front of the target plane 21 may be colored in red while the part of the needle originating from the individual image planes behind the target plane 21 may be colored in blue.

The invention claimed is:

1. A method of imaging a specular object and a target anatomy in a tissue using ultrasound, the method comprising:
   a tissue imaging step comprising:
      transmitting first sound waves into a volumetric region of the tissue, the volumetric region including the target anatomy located in a target plane;
      receiving echoes of said first sound waves from the target plane; and
      processing said received echoes to produce a two-dimensional tissue image;
   a specular object imaging step comprising:
      selecting elevations for imaging the specular object based on an elevation of the target plane used for imaging the target anatomy in the tissue imaging step;
      transmitting second sound waves into said volumetric region of the tissue based on the selected elevations, the volumetric region including the specular object;
      receiving echoes of said second sound waves from a plurality of image planes, said plurality of image planes each corresponding to one of the selected elevations; and
      processing the echoes received from the plurality of image planes to produce a set of two-dimensional specular object images, wherein the method further comprises:
   performing a first combination of the set of two-dimensional specular object images into a first combined two-dimensional specular object image, wherein performing the first combination of the set of two-dimensional specular object images includes coding each of the two-dimensional specular object images based on an elevation position of the two-dimensional specular object image relative to the target plane such that the first combined two-dimensional specular object image indicates a portion of the specular object that is in front of the target plane and a portion of the specular object that is behind the target plane;
   performing a second combination of the two-dimensional tissue image and the first combined two-dimensional specular object image to generate a second combined two-dimensional image; and
   displaying the second combined two-dimensional image.

2. A method as claimed in claim 1, wherein the specular object imaging step is further adapted to segment the specular object out of each individual plane of the plurality of image planes, and to create the specular object image out of the thus segmented individual planes.

3. A method as claimed in claim 1, comprising at least two tissue imaging steps and a least two specular object imaging steps, wherein the tissue imaging steps are performed interleaved with the specular object imaging steps.

4. An ultrasonic imaging apparatus for imaging a specular object and a target anatomy in a tissue, the apparatus comprising:
   an array transducer for transmitting sound waves into a volumetric region of the tissue and for receiving echoes of said sound waves, wherein the array transducer is adapted to have elevation steering capabilities;
   a beamformer
      for controlling the transmission of sound waves by the array transducer such that first sound waves are transmitted into the volumetric region including the target anatomy located in a target plane and echoes are received of said first sound waves from the target plane,
      for selecting elevations for imaging the specular object based on an elevation of the target plane used for imaging the target anatomy, and
      for controlling the transmission of sound waves by the array transducer based on the selected elevations such that second sound waves are transmitted into the volumetric region including the specular object and echoes are received of said second sound waves from a plurality of image planes, said plurality of image planes each corresponding to one of the selected elevations, the selected elevations being distributed in an elevation direction;
   a data processor
      for processing said received echoes of said first sound waves to produce a two-dimensional tissue image, and
      for processing the echoes received from the plurality of image planes to produce a set of two-dimensional specular object images; and
   an image processor
      for performing a first combination of the set of two-dimensional specular object images into a first combined two-dimensional specular object image, wherein performing the first combination of the set of two-dimensional specular object images includes coding each of the two-dimensional specular object images based on an elevation position of the two-dimensional specular object image relative to the target plane such that the first combined two-dimensional specular object image indicates a portion of the specular object that is in front of the target plane and a portion of the specular object that is behind the target plane;

for performing a second combination of the two-dimensional tissue image and the first combined two-dimensional specular object image to generate a second combined two-dimensional image; and for displaying the second combined two-dimensional image.

5. An ultrasonic imaging apparatus as claimed in claim 4, wherein the data processor is further adapted to segment the specular object out of the plurality of image planes.

6. A method as claimed in claim 1, further comprising a segmentation step for performing a three-dimensional segmentation to segment the specular object out of the plurality of image planes.

7. A method as claimed in claim 1, wherein the image planes in the plurality of image planes are being imaged in the specular object imaging step at a lower imaging rate than the imaging rate at which the target plane is being imaged in the tissue imaging step.

8. A method as claimed in claim 1, wherein the set of two-dimensional specular object images includes a two-dimensional specular object image corresponding to the elevation of the target plane.

9. A method as claimed in claim 1, wherein performing the second combination comprises overlaying the first combined two-dimensional specular object image on the two-dimensional tissue image.

10. An ultrasonic imaging apparatus as claimed in claim 4, wherein the set of two-dimensional specular object images includes a two-dimensional specular object image corresponding to the elevation of the target plane.

11. An ultrasonic imaging apparatus as claimed in claim 4, wherein performing the second combination comprises overlaying the first combined two-dimensional specular object image on the two-dimensional tissue image.

12. An ultrasonic imaging apparatus as claimed in claim 4, wherein the selected elevations are between −10 degrees and +10 degrees relative to the elevation of the target plane.

13. An ultrasonic imaging apparatus as claimed in claim 4, wherein the selected elevations for imaging the specular object are centered around the elevation of the target plane.

14. An ultrasonic imaging apparatus as claimed in claim 4, wherein the beamformer is configured to select the elevations for imaging the specular object by:

selecting a central elevation plane coincident with the target plane; and selecting a distribution of elevations centered around the central elevation of the target plane.

15. An ultrasonic imaging apparatus as claimed in claim 4, wherein the beamformer is configured to:

control transmission of the first sound waves using a tissue mode specific set of parameters; and control transmission of the second sound waves using a specular object mode specific set of parameters.

16. An ultrasonic imaging apparatus as claimed in claim 4, wherein the set of two-dimensional specular object images forms a three-dimensional set of images, wherein the data processor is configured to produce the three-dimensional set of images based on the received echoes of the second sound waves, and wherein the set of two-dimensional specular object images correspond to the selected elevations.

* * * * *